(12) United States Patent
Hardaway

(10) Patent No.: US 8,370,173 B2
(45) Date of Patent: *Feb. 5, 2013

(54) SYSTEM AND METHOD FOR DISPERSING MEDICATIONS USING A SINGLE POINT REPLENISHMENT

(75) Inventor: Jason Michael Hardaway, Portland, OR (US)

(73) Assignee: Wellpartner Incorporated, Portland, OR (US)

( * ) Notice: Subject to any disclaimer, the term of this patent is extended or adjusted under 35 U.S.C. 154(b) by 182 days.

This patent is subject to a terminal disclaimer.

(21) Appl. No.: 12/117,447

(22) Filed: May 8, 2008

(65) Prior Publication Data

US 2009/0281823 A1 Nov. 12, 2009

(51) Int. Cl.
G06Q 10/00 (2012.01)
G06Q 50/00 (2012.01)
(52) U.S. Cl. .............................................. 705/2; 705/3
(58) Field of Classification Search ........................ 705/2
See application file for complete search history.

(56) References Cited

U.S. PATENT DOCUMENTS

| | | | | |
|---|---|---|---|---|
| 6,021,392 | A * | 2/2000 | Lester et al. ........................ | 705/2 |
| 6,055,507 | A | 4/2000 | Cunningham | |
| 6,219,587 | B1 | 4/2001 | Ahlin et al. | |
| 7,640,170 | B1 | 12/2009 | Gourley | |
| 7,797,171 | B2 | 9/2010 | Reardan et al. | |
| 7,996,243 | B1 | 8/2011 | Ali et al. | |
| 2001/0037216 | A1 | 11/2001 | Oscar et al. | |
| 2002/0002495 | A1 | 1/2002 | Ullman | |
| 2002/0069088 | A1 | 6/2002 | Berg | |
| 2002/0188469 | A1 | 12/2002 | Shalmi et al. | |
| 2003/0088333 | A1 | 5/2003 | Liff et al. | |
| 2004/0145472 | A1 | 7/2004 | Schmidtberg et al. | |
| 2004/0230502 | A1 | 11/2004 | Fiacco et al. | |
| 2006/0184391 | A1 * | 8/2006 | Barre et al. ........................ | 705/2 |
| 2007/0233517 | A1 | 10/2007 | Dayal | |
| 2007/0233522 | A1 | 10/2007 | Dayal | |
| 2008/0235050 | A1 | 9/2008 | Hallberg | |
| 2008/0288281 | A1 | 11/2008 | Shell et al. | |

OTHER PUBLICATIONS

An Overview of the 340B Drug Discount Program, How to Decrease Medication Costs for Patients,340B Access Solution, 2004 Wellpartner.*
Notice of Allowance for U.S. Appl. No. 12/117,467, filed May 8, 2008, mailed from the USPTO on Sep. 8, 2011, 8 pgs.
Non-final Office Action for U.S. Appl. No. 12/481,449, filed Jun. 9, 2009, mailed from the USPTO on Oct. 6, 2011, 19 pgs.
Non-final Office Action for U.S. Appl. No. 12/117,467, filed May 8, 2008, mailed from the USPTO on Feb. 3, 2011, 11 pgs.
Non-final Office Action for U.S. Appl. No. 12/145,960, filed Jun. 25, 2008, mailed from the USPTO on Apr. 1, 2011, 25 pgs.
Office Action for U.S. Appl. No. 12/552,198, filed May 8, 2008, mailed from the USPTO on Nov. 25, 2011, 19 pgs.

(Continued)

Primary Examiner — Hiep V Nguyen
(74) Attorney, Agent, or Firm — John R. Thompson; Stoel Rives LLP

(57) ABSTRACT

A computer system and methods manages dispensing and replenishment of medications by a Contract Pharmacy for a Covered Entity. Participating Contract Pharmacies are associated with a Covered Entity, and each medication unit is associated with a code that corresponds to medication units dispersed by the Contract Pharmacies. The amount of medication units corresponding to the code and dispersed by the Contract Pharmacies is tracked. When the amount of medication units dispensed across the Contract Pharmacies to patients of the Covered Entity reaches a replenishment threshold, replacement medication units are ordered to replace inventory loaned by the Contract Pharmacies to the Covered Entity at the Covered Entity's available drug discount purchase price.

25 Claims, 3 Drawing Sheets

OTHER PUBLICATIONS

Office Action for U.S. Appl. No. 12/145,960, filed Jun. 25, 2008, mailed from the USPTO on Dec. 12, 2011, 24 pgs.
Anonymous, "GPO Access Solution: An Overview of Group Purchasing and Own Use", 2005, Wellpartner, 31 pgs.
Anonymous, "340B Access Solution: An Overview of the 340B Discount Drug Program", 2004, Wellpartner, 42 pgs.
Anonymous, "Access Solutions," Website printout, archived Jul. 11, 2006, 1 pg.
Office Action for U.S. Appl. No. 12/552,198, filed Sep. 1, 2009, mailed from the USPTO on May 8, 2012, 15 pgs.
Advisory Action for U.S. Appl. No. 12/145,960, filed Jun. 25, 2008, mailed from the USPTO on May 21, 2012, 3 pgs.
Final Office Action for U.S. Appl. No. 12/481,449, filed Jun. 9, 2009, mailed from the USPTO on Jul. 16, 2012, 25 pgs.

* cited by examiner

SYSTEM AND METHOD FOR DISPERSING MEDICATIONS USING A SINGLE POINT REPLENISHMENT

TECHNICAL FIELD

This disclosure relates generally to techniques for managing the replenishment of inventories of dispensing pharmacies, which are loaned to certain covered entities that provide a prescription benefit or program, defined by statute and/or regulation, to a specifically identified class of its patients or benefit plan members.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION OF PREFERRED EMBODIMENTS

Figure 1:
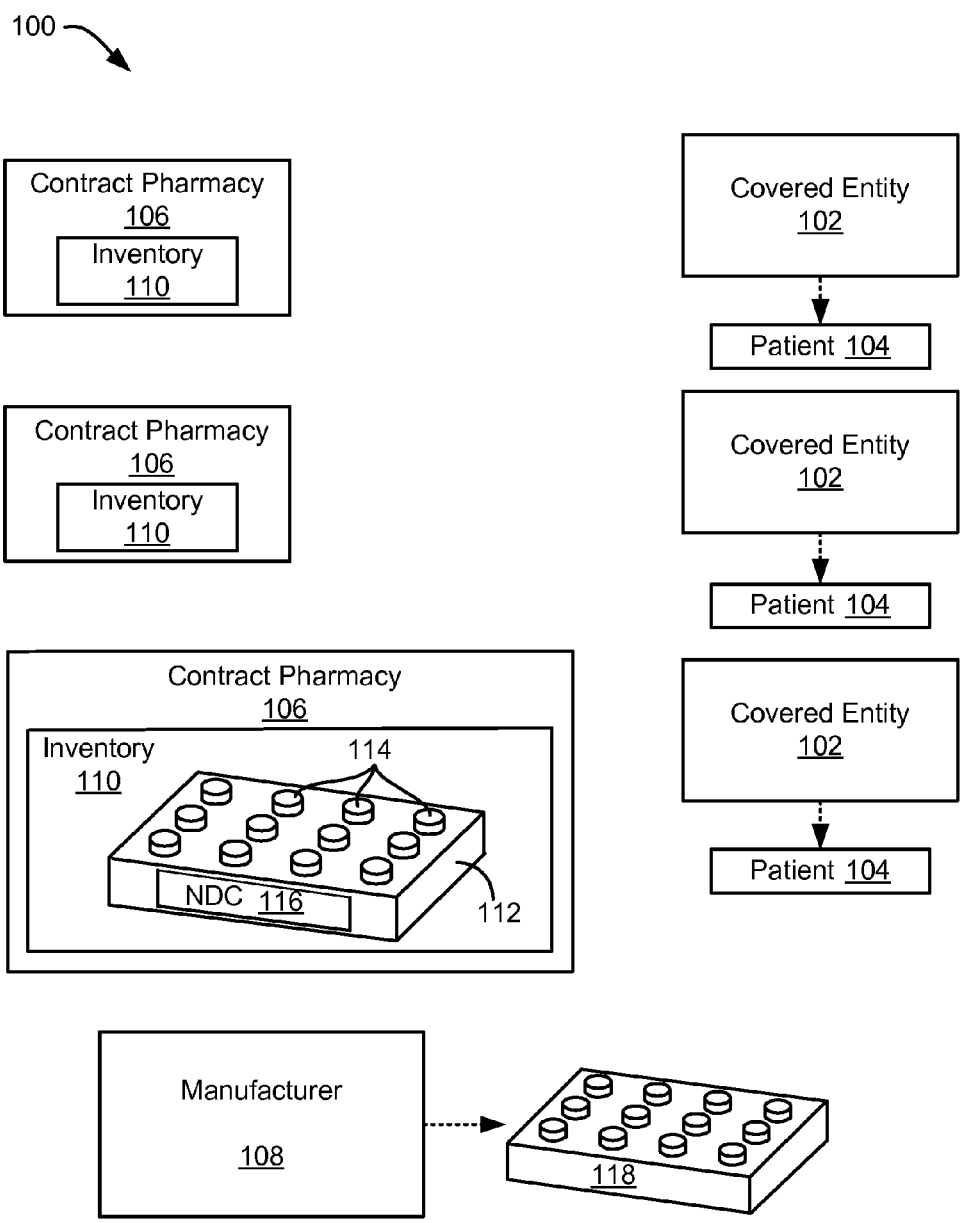
FIG. 1 is a block diagram of a system for distributing prescribed medications.

The described features, structures, or characteristics may be combined in any suitable manner in one or more embodiments. Those skilled in the art will recognize that the invention can be practiced without one or more of the specific details, or with other methods, components, materials, etc. In other instances, well-known structures, materials, or operations are not shown in detail to avoid obscuring aspects of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawing or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable storage medium having stored thereon instructions that may be used to program a computer (or other electronic device) to perform processes described herein. The machine-readable storage medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer may function both as a client and as a server. Each network includes at least two computers, such as the server and/or clients. A computer may be a workstation, laptop computer, disconnectable mobile computer, server, mainframe, cluster, so-called "network computer" or "thin client", personal digital assistant or other hand-held computing device, "smart" consumer electronics device or appliance, or a combination thereof.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, satellites, microwave relays, modulated AC power lines, physical media transfer, and/or other data transmission "wires" known to those of skill in the art. The network may encompass smaller networks and/or be connectable to other networks through a gateway or similar mechanism.

Each computer includes at least a processor and a memory; computers may also include various input devices and/or output devices. The processor may include a general purpose device, such as a 80.times.86, Pentium (mark of Intel), 680.times.0, or other "off-the-shelf" microprocessor. The processor may include a special purpose processing device, such as an ASIC, PAL, PLA, PLD, Field Programmable Gate Array, or other customized or programmable device. The memory may include static RAM, dynamic RAM, flash memory, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computers may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as: general purpose computers; computer programming tools and techniques; computer networks and networking technologies; digital storage media; authentication, access control, and other security tools and techniques provided by public keys, encryption, firewalls, and/or other means.

Referring to FIG. 1, a block diagram of participants in a system 100 for dispersing and replenishing medications is shown. A plurality of health care entities (Covered Entities) 102 are shown which provide a pharmacy benefit or program for patients 104. Medications are dispensed to the patients 104 by pharmacies (Contract Pharmacies) 106 under the supervision of a Covered Entity 102. The Contract Pharmacies 106 may provide medications to the Covered Entity 102 or may provide medications directly to the patients 104. The Contract Pharmacies 106 replenish medication inventories from manufacturers 108. As can be appreciated, a wide variety of programs may be involved in providing health care services and dispersing medications, and these programs often impact pricing.

One federal program is the 340B program, also known as the section 602 or "PHS" pricing. It is a federally administered program that allows certain qualified Covered Entities 102 within the health care safety-net to purchase out-patient medications from manufacturers 108 at or below a defined discount price. It is important to note that the 340B program is not a governmental purchasing program but is a discount program administered by the federal government. Pharmaceutical manufacturers 108 are required to sell covered medications to certain Covered Entities 102 at or below a statutorily defined "ceiling price" as a condition for Medicaid participation. The 340B price is the ceiling price, meaning it is the most that Covered Entities 102 can be charged for medications purchased directly from manufacturers 108. In compliance with statutes, the ceiling price is derived from Medicaid pricing. Covered Entities 102 are allowed, and even encouraged, to negotiate sub-ceiling prices with manufacturers 108. In addition to providing a pricing structure for safety-net entities, the 304B program establishes eligibility requirements for Covered Entities 102. Thus, the Covered Entities 102 are able to realize substantial cost reductions on medications used for patients 104 in an out-patient setting. Covered medications may include any medication reimbursed by Medicaid, including prescription or over-the-counter medications.

Eligibility for Covered Entities 102 is established by federal statute, and eligible Covered Entities 102 include recipients of certain federal grants. Eligibility for participation in a 340B program is determined by entities' status, specifically by receiving one of several grants or by being a certain type of disproportionate-share hospital or federally qualified health center (FQHC) or look-alike. Covered Entities 102 include core safety-net entities and a number of health facilities. Various FQHCs may be eligible Covered Entities 102, such as consolidated health centers, migrant health centers, health care for the homeless, school-based health centers, public housing health centers, PL 93-638 tribal health centers, urban Indian health centers, and qualified community health clinics. Other eligible entities may also include FQHC look-alikes, native Hawaiian health centers, Ryan White Care Act Grantees, Title X Family Planning, black lung clinics, comprehensive hemophilia diagnostic treatment centers, state or locally funded centers treating sexually transmitted diseases or tuberculosis, certain disproportionate-share hospitals, and other safety-net organizations.

A patient who receives medication through a 340B program must be an out-patient 104 of a Covered Entity 102. This requirement prevents against the risk of diversion of 340B program products to non-qualified patients. The 340B program prohibits all forms of medication resale or diversion. Diversion is the distribution of 340B medications to non-340B eligible patients, either intentionally or unintentionally. The Covered Entity 102 may not resell or transfer the drug to a person who is not a patient of the Covered Entity 102.

The 340B program further prohibits "double-dipping." Covered Entities 102 cannot request 340B prices for the same medication for which a State Medicaid agency will request a rebate under the OBRA 1990 rebate mechanism. With this prohibition, a Covered Entity 102 can receive a discount through the 340B program, or a State Medicaid agency can receive a discount via rebate. However, both may not occur for the same medication.

Covered Entities 102 may provide 340B pharmacy access for their patients through one of three methods. A first method is a clinic dispensary, which is an on-site dispensing cabinet utilizing a small inventory of basic medications. A second method is a full-service, in-house pharmacy created and operated by the Covered Entity 102 on its premises. A third method is a contracted pharmacy (Contract Pharmacy) 106, which is an external pharmacy under contract with the Covered Entity 102 to provide pharmacy services and medications to the Covered Entity 102 and/or entity's patients. Since the 340B program is an entity-specific medication discount program, the entity is the only organization that can legally purchase 340B medications. Therefore, a Contract Pharmacy 106 must operate under a "bill-to/ship-to" arrangement, where medications are shipped by the drug wholesaler directly to the Contract Pharmacy 106, and the bill for the medications is sent to the Covered Entity 102.

When dispensing medications to patients, including patients 104 of the Covered Entities 102, Contract Pharmacies 106 may operate using a "replenishment model." The replenishment model is used in the 340B program and, in one implementation, enables Contract Pharmacies 106 to manage their 340B inventory virtually while receiving 340B replacement product on a replenishment basis. In one implementation, the replenishment model provides a form of inventory control. The replenishment model allows a Contract Pharmacy 106 to dispense medication to 340B covered patients 104 from its own inventory 110, and then have that inventory 110 replenished by the Covered Entity 102. In effect, the Contract Pharmacy 106 "loans" the Covered Entity 102 the medication, and the Covered Entity 102 then orders replacement inventory. The advantage of this approach is that it reduces the likelihood of medication diversion as there is no specific 340B inventory sitting on the Contract Pharmacy's 106 shelves. Another method of inventory control involves maintaining a separate physical inventory. However, the replenishment model is very effective in preventing diversion and double-dipping while also providing an option for reduced costs.

In an inventory 110, containers 112 include a quantity of medication units 114. The medication units 114 are discrete units and may be dispensed to patients 104 and/or the Covered Entity 102. A container 112 will have a corresponding national drug code (NDC) 116 that identifies the type of medication and the number of medication units 114. Typically, the number of medication units in an NDC 116 remains unchanged. Under the replenishment model, inventory replenishment may include determining the quantity of medication units 114 corresponding to and dispensed from a particular NDC 116.

A Covered Entity 102 orders a replacement container 118 from a manufacturer 108 when the number of dispensed medication units 114 for the original container 112 and the NDC 116 meets or exceeds a replenishment threshold. The replenishment threshold is typically the number of medication units 114 in both the original and the replacement containers 112, 118, and that number is also reflected in the corresponding NDC 116.

A difficulty arises when, after a certain time period, the number of dispensed medication units does not equal the number of medication units 114 in that particular NDC 116. As can be expected, after a certain time interval, a Contract Pharmacy 106 desires to replenish the inventory 110 that it has dispensed to patients 104 of the Covered Entity 102. A Contract Pharmacy 106 may desire this replenishment even though a replenishment threshold has not yet been met for a container 112. Thus, after a time period, a Contract Pharmacy 106 may have a policy of automatically replenishing an NDC 116. This automatic replenishment after a certain time period is referred to herein as "trueing-up." The time period may be any number of days, weeks, or months that a Contract Pharmacy 106 sets as its policy.

When a true-up occurs, the Covered Entity 102 is charged the replacement cost of the dispensed medication units at the Contract Pharmacy's 106 acquisition price. The acquisition price may be significantly greater than a price under the 340B program (or other program) of the Covered Entity 102. This can lead to significantly increased costs for the Covered Entity 102. A further point of complexity is that, if the Covered Entity 102 has a number of contract pharmacies 106, then the risk of "true-ups" occurring increases proportional to the number of additional Contract Pharmacies 106 participating. As can be appreciated, with multiple Contract Pharmacies 106, there is an increased risk of partially depleted containers occurring after a predetermined time period.

Figure 2:
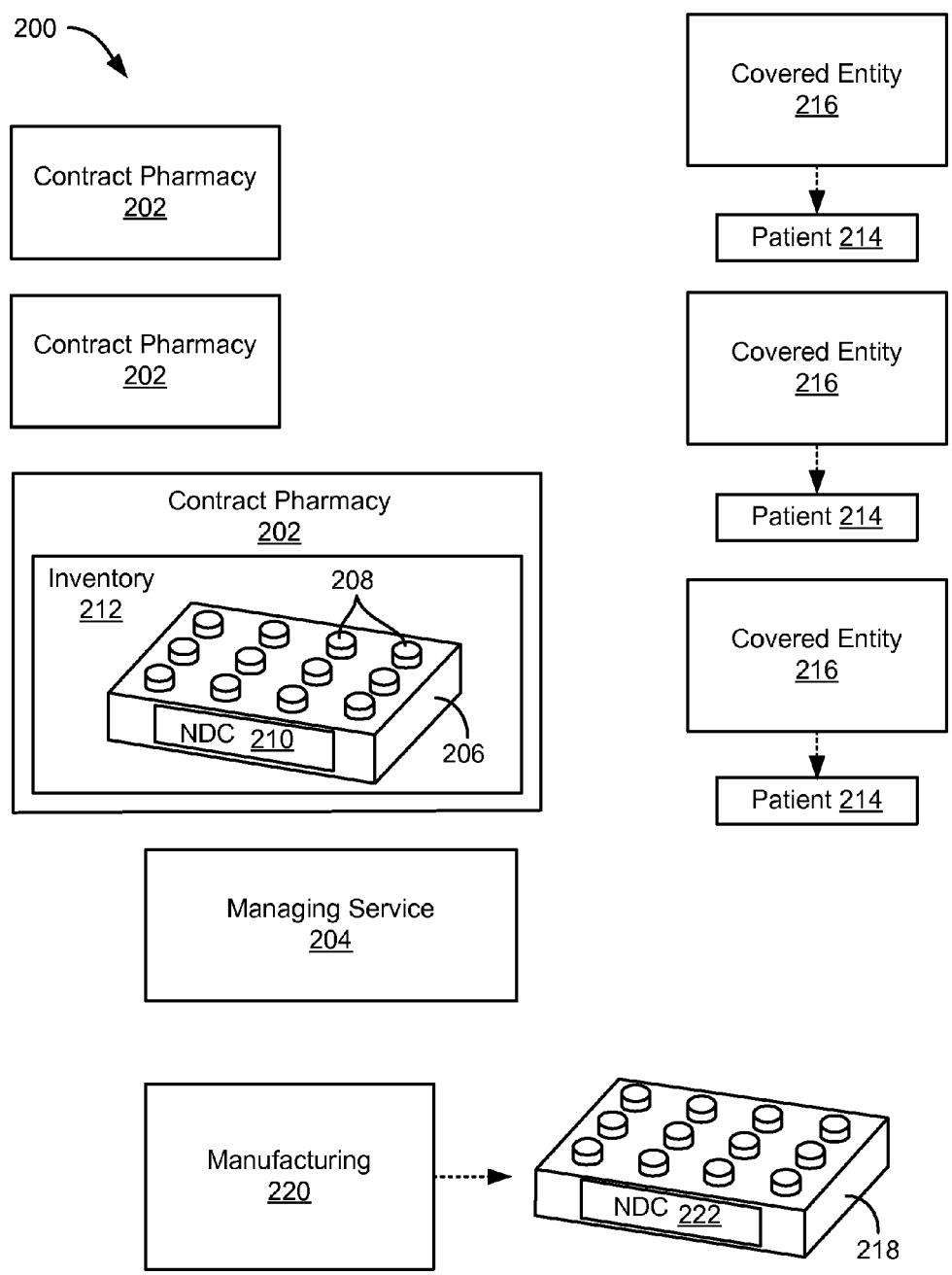
FIG. 2 is a block diagram of a system for distributing prescribed medications.

Referring to FIG. 2, a block diagram of a system 200 for dispersing medications through a single point replenishment is shown. The system 200 minimizes the risk of "true-ups" by using a plurality of associated, participating Contract Pharmacies 202. The Contract Pharmacies 202 may be associated with one another through any number of relationships, such as contractual or ownership relationships. For example, the Contract Pharmacies 202 may have contractual agreements with one another or be members of the same company, franchise, chain, or be affiliated in some other manner. A managing service 204 is in communication with each participating Contract Pharmacy 202 and tracks containers 206, corresponding medication units 208, and corresponding NDCs 210 that are in the Contract Pharmacies' 202 inventories 212. Communication may be enabled through a computer network system.

The managing service 204 tracks filled and dispensed prescriptions across all of the related Contract Pharmacies 202. By filling prescriptions, medication units 208 are dispensed to patients 214 of Covered Entities 216. The managing service 204 determines when the combined number of all of the medication units 208 for all of the prescriptions dispensed from all of the related Contract Pharmacies 202 reaches the replenishment threshold of a particular NDC 210. When the replenishment threshold is reached, the managing service 204 orders a replacement container 218 from a manufacturer 220. The replacement container 218 is credited to the related Contract Pharmacies 202 collectively as opposed to an individual Contract Pharmacy 202. The related Contract Pharmacies 202 collectively take ownership of the replacement container 218. The Contract Pharmacies 202 may combine their dispensing from this container 218 and its associated NDC 222.

The manner of dispersing from the replacement container 218 and NDC 222 may be performed by the related Contract Pharmacies 202 in various ways. For example, the replacement container 218 and NDC 222 may be assigned to one holding Contract Pharmacy 202, and medication units 208 may be distributed from the holding Contract Pharmacy 202. In yet another technique, the medication units 208 may also be divided disproportionately based on historical use or some other distribution scheme. In addition to distribution, one Contract Pharmacy 202 may be assigned to the NDC 222 for purposes of administration. One of skill in the art will appreciate that all such dispersing methods between Contract Pharmacies 202 are included within the scope of the disclosure. The managing service 204 provides the oversight and resources to ensure that the 340B program is successfully implemented and administered on behalf of the Covered Entity 216.

Figure 3:
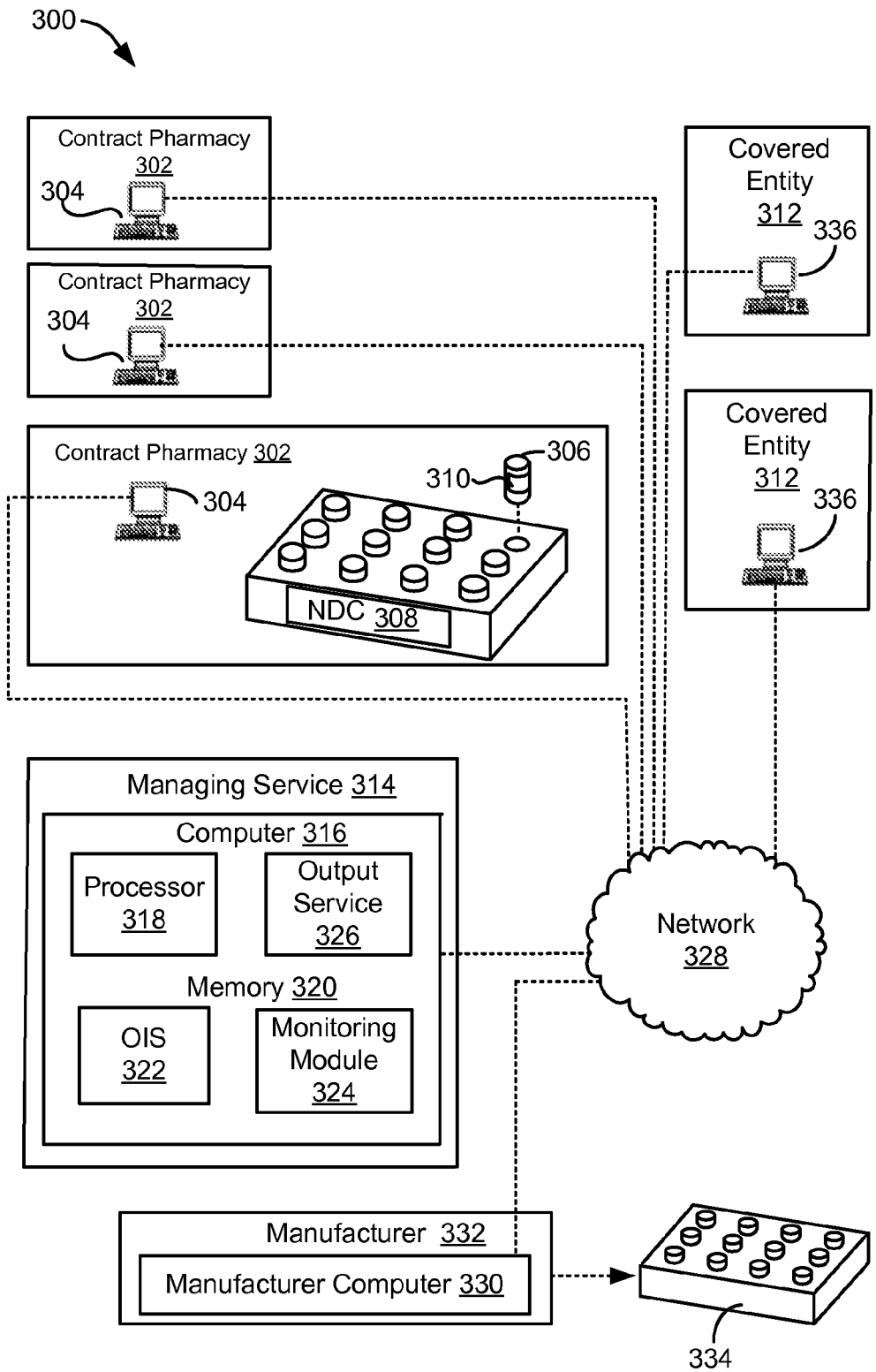
FIG. 3 is a block diagram of another system for distributing prescribed medications.

Referring to FIG. 3, a system 300 for tracking medication dispersals using a single point replenishment is shown. Each participating Contract Pharmacy 302 may include one or more computers 304 to record a dispersal of a medication unit 306 corresponding to an NDC 308. Input to a computer 304 to record and track a medication unit dispersal may be performed in a variety of ways including manual entry, such as by typing an identifier through use of a keyboard, or optical scanning technology.

In one embodiment, bar code technology may be used to track prescriptions and medication units 306 throughout the fulfillment process. Each medication unit 306 may include a corresponding bar code 310 which is disposed on the unit 306. The bar code 310 may include information as to the type of medication, the corresponding NDC 308, the amount of medication, the cost, etc. An optical scanner or other device used for scanning may be in electrical communication with the computer 304 through any one of a number of conventional networks. A prescription may also include a bar code which includes information on the type of medication, the prescription refills, the Covered Entity 312, and other relevant information. When a prescription is filled, the prescription may be scanned and prescription information may be stored in the computer 304. Similarly, the corresponding medication unit 306 may be scanned, and corresponding medication unit information may be stored in the computer 304. The NDC 308 may also be scanned and the code entered into the computer 304. Scanning the NDC 308 may involve reading the code on a storage container.

A Contract Pharmacy 302 may have a plurality of computers 304 which are in electrical communication with one another through a network. A Contract Pharmacy 302 may also include a database (not shown) for storing prescription, medication unit information, and the NDC 308.

A managing service 314 may include a computer 316 comprising a processor 318 and a memory 320 including any of the embodiments discussed above. The memory 320 may include an operating system 322 and a monitoring module 324 to track the dispersal of medication units 306 and determine when the dispersal reaches a replenishment threshold.

The managing service computer 316 may be in electrical communication with the Contract Pharmacy 302 computers 304 through a network 328. The managing service computer 316 associates the participating Contract Pharmacies 302 with the NDC 308 that corresponds to medication units 306 being dispersed. The monitoring module 324 tracks the amount of dispersed medication units 306 and determines when the replenishment threshold is reached. In one embodiment, upon reaching the replenishment threshold, the managing service computer 316 may notify a user through an output device 326. The output device 326 may include a monitor or display running a suitable graphical user interface to thereby notify a user. Notification may also be performed through a variety of other techniques including email, updating a record in a database, hardcopy printout, updating a spreadsheet, and the like.

The managing service computer 316 may be in electrical communication through the network 328, or another network, with a manufacturer computer 330 of a manufacturer 332. When a replenishment threshold corresponding to an NDC 308 is reached, the managing service computer 316 may notify the manufacturer computer 330 and place an order for a replacement NDC 334. The replacement NDC 334 typically comprises a replacement container with the same number of medication units 306. In this manner, an NDC 308 is replaced expeditiously, and the risk of a true-up situation is minimized.

The managing service computer 316 may further be in electrical communication with one or more health care entity computers 336 of a Covered Entity 312. The managing service computer 316 may inform a health care entity computer 336 of when a prescription is received at a participating Contract Pharmacy 302, when the prescription is filled, and the medication unit 306 that is dispensed. An Covered Entity 312 is thereby informed of the status of prescriptions provided to its covered patients. If desired, the Covered Entity 312 may also be informed as to the replenishment of an NDC 308. As disclosed herein, the system 300 is able to ensure compliance with the 340B program and avoid true-up situations.

The managing service computer 316 may further maintain an account corresponding to the NDC 308 and the Contract Pharmacies 302. The account may include information regarding the dispersal of the medication units 306, a charge associated with the dispersal of each medication unit 306, orders for replacement NDCs 334 corresponding to the NDC 308, and the charge associated with the dispersal of each replacement NDC 334. The managing service computer 316 may determine each Covered Entity's 312 share of cost for the replacement NDC 334. As can be appreciated, calculating share of cost may be determined in a variety of ways. The managing service computer 316 may further generate an invoice for each participating Contract Pharmacy 302 to convey the share of cost. The invoice may be communicated to each Contract Pharmacy 302 over the network 328.

As disclosed herein, a Covered Entity 312 is able to contract with multiple Contract Pharmacies 302 while minimizing the overall costs associated with a "true-up" situation. Thus, the benefits of participating in a 340B program may be more fully realized. After Contract Pharmacies 302 collectively reach replenishment threshold for an NDC 222, a managing service orders a replacement container for the corresponding NDC 222.

It will be obvious to those having skill in the art that many changes may be made to the details of the above-described embodiments without departing from the underlying principles of the disclosure.

What is claimed is:

1. A computer system to manage replenishment of medications loaned to a covered entity by a plurality of independent contract pharmacies providing services to patients of the covered entity,
   the plurality of independent contract pharmacies dispensing medication units from a common inventory to,
      patients who do not qualify to receive discounted medication units under the regulatory scheme of the covered entity, and
      covered patients of the covered entity who qualify to receive discounted medication units under the regulatory scheme of the covered entity, wherein medication units dispensed to the covered patients are to be replenished by the covered entity, and wherein the dispensed medication units are associated with a national drug code ("NDC");
   wherein the covered entity is entitled to purchase discounted medication for covered patients under a regulatory scheme, and wherein the independent contract pharmacies are not entitled to purchase discounted medication units under the regulatory scheme, the system comprising:
   a central managing service in communication with each of the independent contract pharmacies, comprising:
      a processor;
      an output device in electrical communication with the processor; and
      a monitoring module component operating on the processor to perform the method of,
         identifying an amount of medication units of the NDC dispensed from a respective common inventory by each of the plurality of independent contract pharmacies to covered patients of the covered entity, wherein the covered entity is to replenish the identified medication units;
         calculating a combined amount of medication units of the NDC dispensed across the plurality of independent contract pharmacies by summing together the amount of medication units of the NDC dispensed to the covered patients by each of the plurality of independent contract pharmacies, wherein the combined amount of medication units is to be replenished by the covered entity;
         determining when the combined amount of medication units reaches a replenishment threshold, wherein the replenishment threshold is based on the NDC of the identified medication units; and
         upon the combined amount reaching the replenishment threshold, replenishing the identified medication units by,
            purchasing a discounted replacement container of medication units corresponding to the NDC under the regulatory scheme of the covered entity, the replacement container comprising medication units to replenish the combined amount of identified medication units dispensed to covered patients across the plurality of independent contract pharmacies, and transferring ownership of the replacement container to the independent contract pharmacies.

2. The system of claim 1, wherein the monitoring module component identifies the medication units dispensed by the independent contract pharmacies using the NDC.

3. The system of claim 2, wherein the NDC identifies a type of medication and a quantity of medication units in a container.

4. The system of claim 1, wherein the method performed by the monitoring module component further comprises:

upon reaching the replenishment threshold, instructing the output device to provide notification to a user.

5. The system of claim 1, wherein the independent contract pharmacies have a business relationship with each other.

6. The system of claim 1, wherein the covered entity is eligible to purchase reduced cost medication under a statutorily defined program to thereby enable purchase of the discounted replacement container at a reduced cost directly from a manufacturer, and wherein the independent contract pharmacies are not eligible to purchase the discounted replacement container at the reduced cost under the statutorily defined program.

7. The system of claim 1, wherein identifying medication units of the NDC dispensed to covered patients includes reading bar codes corresponding to dispensed medication units.

8. The system of claim 7, wherein identifying medication units of the NDC dispensed to covered patients includes communicating with the independent contract pharmacies over a network.

9. A computer readable storage medium, having stored thereon computer readable instruction code for performing a method to replenish medications loaned to a covered entity by a plurality of independent contract pharmacies providing services to patients of the covered entity, wherein each of the independent contract pharmacies dispense medication units from a common inventory to, patients who do not qualify to receive discounted medication units under the regulatory scheme of the covered entity, and covered patients of the covered entity who qualify to receive discounted medication units under the regulatory scheme of the covered entity, wherein medication units dispensed to the covered patients are to be replenished by the covered entity, and wherein the dispensed medication units are associated with a national drug code ("NDC");

wherein the covered entity is entitled to purchase discounted medication for covered patients under a regulatory scheme, wherein the independent contract pharmacies are not entitled to purchase discounted medication units under the regulatory scheme, the method comprising:

identifying an amount of medication units of the NDC dispensed from a respective common inventory by each of the plurality of independent contract pharmacies to covered patients of the covered entity, wherein the covered entity is to replenish the identified medication units;

calculating a combined amount of medication units of the NDC dispensed across the plurality of independent contract pharmacies by summing together the amount of medication units of the NDC dispensed to the covered patients by each of the plurality of independent contract pharmacies, wherein the combined amount of medication units is to be replenished by the covered entity;

determining when the combined amount of medication units reaches a replenishment threshold, wherein the replenishment threshold is based on the NDC of the identified medication units; and upon the combined amount reaching the replenishment threshold, replenishing the identified medication units by, purchasing a discounted replacement container of medication units corresponding to the NDC under the regulatory scheme of the covered entity, the replacement container comprising medication units to replenish the combined amount of identified medication units dispensed to covered patients across the plurality of independent contract pharmacies, and transferring ownership of the replacement container to the independent contract pharmacies.

10. The computer readable storage medium of claim 9, wherein the medication units dispensed to the covered patients by the independent contract pharmacies are identified using the NDC.

11. The computer readable storage medium of claim 10, wherein the NDC identifies a type of medication and a quantity of medication units in a container.

12. The computer readable storage medium of claim 9, wherein the method further comprises:

upon reaching the replenishment threshold, providing notification to a user.

13. The computer readable storage medium of claim 9, wherein the independent contract pharmacies have a business relationship with each other.

14. The computer readable storage medium of claim 9, wherein the covered entity is eligible to purchase reduced cost medication under a statutorily defined program to thereby enable purchase of the discounted replacement container at a reduced cost directly from a manufacturer, and wherein the independent contract pharmacies are not eligible to purchase the discounted replacement container at the reduced cost under the statutorily defined program.

15. The computer readable storage medium of claim 9, wherein identifying medication units of the NDC dispensed to covered patients includes reading bar codes corresponding to dispensed medication units.

16. The computer readable storage medium of claim 15, wherein identifying medication units of the NDC dispensed to covered patients includes communicating with the independent contract pharmacies over a network.

17. A method of managing replenishment of medications loaned to a covered entity by a plurality of independent contract pharmacies providing services to patients of the covered entity, wherein each of the independent contract pharmacies dispense medication units from a common inventory to, patients who do not qualify to receive discounted medication units under the regulatory scheme of the covered entity, and covered patients of the covered entity who qualify to receive discounted medication units under the regulatory scheme of the covered entity, wherein medication units dispensed to the covered patients are to be replenished by the covered entity, and wherein the dispensed medication units are associated with a national drug code ("NDC");

wherein the covered entity is entitled to purchase discounted medication for covered patients under a regulatory scheme, wherein the independent contract pharmacies are not entitled to purchase discounted medication units under the regulatory scheme, the method comprising:
- identifying, by a computing device, an amount of medication units of the NDC dispensed from a respective common inventory by each of the plurality of independent contract pharmacies to covered patients of the covered entity, wherein the covered entity is to replenish the identified medication units;
- calculating a combined amount of medication units of the NDC dispensed across the plurality of independent contract pharmacies by summing together the amount of medication units of the NDC dispensed to the covered patients by each of the plurality of independent contract pharmacies, wherein the combined amount of medication units is to be replenished by the covered entity;
- determining, by the computing device, when the combined amount of medication units reaches a replenishment threshold, wherein the replenishment threshold is based on the NDC of the identified medication units; and
- upon the combined amount reaching the replenishment threshold, replenishing the identified medication units by,
  - purchasing a discounted replacement container of medication units corresponding to the NDC under the regulatory scheme of the covered entity, the replacement container comprising medication units to replenish the combined amount of identified medication units dispensed to covered patients across the plurality of independent contract pharmacies, and
  - transferring ownership of the replacement container to the independent contract pharmacies.

18. The method of claim 17, wherein identifying comprises identifying the medication units dispensed by the independent contract pharmacies using the NDC.

19. The method of claim 18, wherein the NDC identifies a type of medication and a quantity of medication units in a container.

20. The method of claim 17, further comprising:
- upon reaching the replenishment threshold, providing notification to a user.

21. The method of claim 17, wherein the independent contract pharmacies have a business relationship with each other.

22. The method of claim 17, wherein the covered entity is eligible to purchase reduced cost medication under a statutorily defined program to thereby enable purchase of the discounted replacement container at a reduced cost directly from a manufacturer, and wherein the independent contract pharmacies are not eligible to purchase the discounted replacement container at the reduced cost under the statutorily defined program.

23. The method of claim 17, wherein identifying medication units of the NDC dispensed to covered patients includes reading bar codes corresponding to dispensed medication units.

24. The method of claim 23, wherein identifying medication units of the NDC dispensed to covered patients includes communicating with the independent contract pharmacies over a network.

25. A method of managing replenishment of medications loaned to a covered entity by a plurality of independent contract pharmacies providing services to patients of the covered entity, the method comprising:
- providing, by a computing device, for each of the plurality of independent contract pharmacies dispensing medication units from a common inventory to
  - patients who do not qualify to receive discounted medication units under the regulatory scheme of the covered entity, and
  - covered patients of the covered entity who qualify to receive discounted medication units under the regulatory scheme of the covered entity, wherein medication units dispensed to the covered patients are to be replenished by the covered entity, and wherein the dispensed medication units are associated with a national drug code ("NDC");
- wherein the covered entity is entitled to purchase discounted medication for covered patients under a regulatory scheme, and wherein the independent contract pharmacies are not entitled to purchase discounted medication units under the regulatory scheme;
- identifying, by a computing device, an amount of medication units of the NDC dispensed from a respective common inventory by each of the plurality of independent contract pharmacies to covered patients of the covered entity, wherein the covered entity is to replenish the identified medication units;
- calculating a combined amount of medication units of the NDC dispensed across the plurality of independent contract pharmacies by summing together the amount of medication units of the NDC dispensed to the covered patients by each of the plurality of independent contract pharmacies, wherein the combined amount of medication units is to be replenished by the covered entity;
- determining, by the computing device, when the combined amount of medication units of the NDC reaches a replenishment threshold, wherein the replenishment threshold is based on the NDC of the identified medication units; and
- upon reaching the replenishment threshold, replenishing the identified medication units by,
  - providing a payment from the covered entity to a manufacturer for a discounted replacement container of medication units corresponding to the NDC under the regulatory scheme of the covered entity, the replacement container comprising medication units to replenish the combined amount of identified medication units dispensed to covered patients across the plurality of independent contract pharmacies, and
  - providing for the manufacturer shipping the replacement container directly to one of the plurality of independent contract pharmacies.

* * * * *